United States Patent [19]

Sugamiya et al.

[11] 4,383,121

[45] May 10, 1983

[54] PROCESS FOR PURIFYING MONOCHLOROACETIC ACID

[75] Inventors: Ryoji Sugamiya, Yachio; Kazuto Nakamaru, Kashiwa; Keizo Takegami, Kamakura; Koji Miwa, Yokohama; Minoru Morita, Kodaira, all of Japan

[73] Assignee: Tsukishima Kaikai Co., Ltd., Tokyo, Japan

[21] Appl. No.: 223,946

[22] Filed: Jan. 12, 1981

[30] Foreign Application Priority Data

Jan. 16, 1980 [JP] Japan ................................. 55-2638

[51] Int. Cl.³ ............................................ C07C 51/43
[52] U.S. Cl. ................................ 562/602; 562/603
[58] Field of Search .............................. 562/602, 603

[56] References Cited

U.S. PATENT DOCUMENTS

| | | | |
|---|---|---|---|
| 2,539,238 | 1/1951 | Eaker | 260/539 |
| 2,809,214 | 10/1957 | Haimsohn | 562/602 |
| 3,365,493 | 1/1968 | Line | 562/602 |

FOREIGN PATENT DOCUMENTS

| | | | |
|---|---|---|---|
| 552754 | 2/1958 | Canada | 562/603 |
| 748950 | 12/1966 | Canada | 562/602 |
| 2110373 | 9/1972 | Fed. Rep. of Germany | 562/603 |
| 43-22572 | 9/1968 | Japan. | |
| 949393 | 2/1964 | United Kingdom. | |

Primary Examiner—Michael L. Shippen
Attorney, Agent, or Firm—Armstrong, Nikaido, Marmelstein & Kubovcik

[57] ABSTRACT

A mixture containing monochloroacetic acid and dichloroacetic acid as the main components are admixed with 5–25% by weight of water on the basis of sum total of monochloroacetic acid, dichloroacetic acid and water, and subjected to adiabatic cooling under a pressure of 133 to 2,660 Pa, whereby monochloroacetic acid is crystallized with a high purity.

2 Claims, 2 Drawing Figures

PROCESS FOR PURIFYING MONOCHLOROACETIC ACID

This invention relates to a process for purifying monochloroacetic acid.

Monochloroacetic acid is generally produced by chlorination of acetic acid, wherein dichloroacetic acid and trichloroacetic acid are inevitably produced as by-products, and usually the resulting reaction product solution contains 80-85% by weight of monochloroacetic acid, 2-5% by weight of dichloroacetic acid, and 10-18% by weight of acetic acid and acetyl chloride.

Heretofore, monochloroacetic acid has been purified by crystallization of monochloroacetic acid, that is, separating acetic acid and acetyl chloride from the reaction product solution by distillation, and cooling the resulting crude monochloroacetic acid comprising monochloroacetic acid, dichloroacetic acid and acetic acid by cooling, thereby crystallizing out monochloroacetic acid therefrom. Monochloroacetic acid is generally crystallized by indirect cooling, that is, by indirectly removing the sensible heat of the solution and the heat of crystallization through a heat transfer surface. The indirect cooling requires the heat transfer surface and thus the production of crystals per unit volume of a crystallizer is small, and also crystals deposit on the heat transfer surface. Thus, it is necessary to prevent the deposition of crystals on the heat transfer surface. Furthermore, the operation is inevitably batchwise, and automation of the operation is impossible. Thus, many technically difficult problems as to controlling of constant cooling rate and stable stirring state, etc. are involved therein.

It is known that in the crystallization larger grain size and higher crystal purity are attained by adding water or an organic solvent such as carbon tetrachloride, trichlorethylene and perchlorethylene to the solution. For example, U.S. Pat. No. 2,809,214 discloses that monochloroacetic acid is crystallized by ading 3-4% by weight of carbon tetrachloride or water to the solution, followed by indirect cooling, whereby grain size of 0.1-0.5 mm is obtained.

Japanese Patent Publication No. 22572/68 discloses a process for crystallizing monochloracetic acid by adiabatic cooling, that is, by converting the sensible heat of the solution and the heat of crystallization to the latent heat of evaporation by reducing the operating pressure of the crystallizer to vacuum, where a solution comprising 90-99% by weight of monochloroacetic acid, 0-5% by weight of dichloroacetic acid and 0-3% by weight of acetic acid is admixed with 0.01-0.5% by weight of water on the basis of sum total of the solution and the water, the resulting mixed solution is further admixed with about 70% by weight of an organic solvent such as methylene chloride, etc. on the basis of sum total of the mixed solution and the organic solvent, and then the resulting solution is subjected to adiabatic cooling to $-20°\text{--}40°$ C., whereby crystals of monochloroacetic acid are obtained. The process uses an organic solvent, and thus requires drying of crystals and recovery of the organic solvent from the resulting mother liquor. Furthermore, some of the organic solvent is lost, and thus operating cost is disadvantageously increased. Furthermore, monochloroacetic acid is a starting material for carboxymethyl cellulose (CMC), which is used as a food additive, and thus it is not desirable that even a trace of the organic solvent remains in the crystals of monochloroacetic acid. That is, the process using an organic solvent is not desirable.

The present invention provides a process for crystallizing out monochloroacetic acid from a mixture containing monochloroacetic acid and dichloroacetic acid as the main components by adiabatic cooling only by addition of 5-25% by weight of water on the basis of sum total of monochloroacetic acid, dichloroacetic acid and water without using any organic solvent. The present process requires no heat transfer surface for the intended crystallization, and can be carried out with continuous operation and a larger production of crystals per unit volume of a crystallizer. Since no organic solvent is used, it is not necessary to carry out drying of crystals.

According to the present invention, 5-25% by weight of water is added to a solution comprising 0-3% by weight of acetic acid, 90-99% by weight of monochloroacetic acid, and 1-6% by weight of dichloroacetic acid on the basis of sum total of monochloroacetic acid, dichloroacetic acid and water, and the resulting solution is subjected to adiabatic cooling under a pressure of 133-2660 Pa. When a ratio of water to the mixture of monochloroacetic acid and dichloroacetic acid is constant in that case, a constant boiling point is given under a given pressure, and monochloroacetic acid is crystallized out according to a solid-liquid equilibrium curve in the system at the corresponding temperature. Vapor generated by the adiabatic cooling is a mixture of monochloroacetic acid, dichloroacetic acid, and water, and the condensate of the vapor does not crystallize at the condensation temperature. When the monochloroacetic acid in the generated vapor is discharged from the system as a waste, the monochloroacetic acid yield is deteriorated, and thus all the condensate is preferably refluxed to the crystallizer.

The present invention will be described in detail below, referring to the accompanying drawings.

Figure 1:
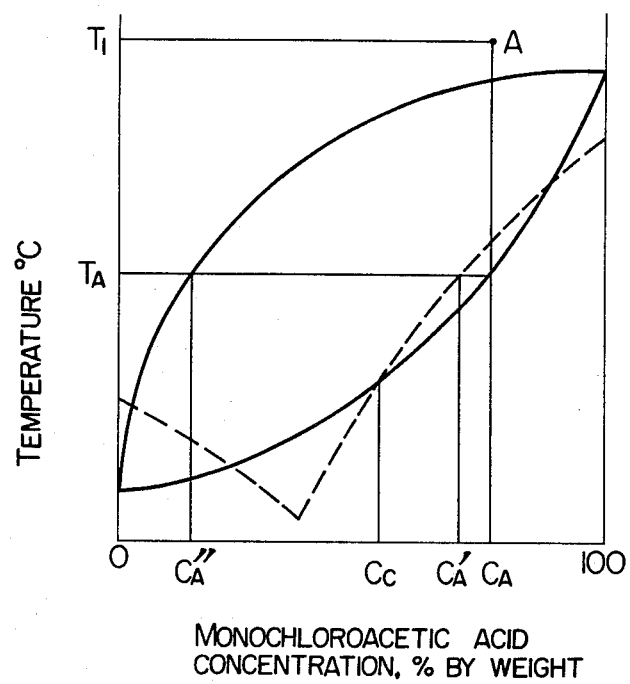
FIG. 1 is a diagram explaining the principle of the present invention, where the vapor-liquid equilibrium curves of a solution consisting of monochloroacetic acid, dichloroacetic acid and water are plotted by full line, and a solid-liquid equilibrium curve is plotted by dotted line, on the presumption that a ratio of dichloroacetic acid to water is constant.

In FIG. 1, vapor-liquid equilibrium curves (full lines) and a solid-liquid equilibrium curve (dotted line) of a system of monochloroacetic acid-dichloroacetic acid-water under a given pressure are shown. Since the ratio of dichloroacetic acid to water in mother liquor is constant when monochloroacetic acid is crystallized by adiabatic cooling, the diagram is prepared on the presumption that the ratio of dichloroacetic acid to water is constant.

In FIG. 1, a solution A having a concentration of monochloroacetic acid, CA % by weight, and a concentration of water and dichloroacetic acid, (1-CA) % by weight, at a temperature $T_1$ is subjected to adiabatic cooling under a pressure given between 133 and 2,660 Pa. If the temperature of the solution is lowered to TA by adiabatic cooling, the concentration of monochloroacetic acid in the liquid phase is CA % by weight according to the vapor-liquid equilibrium curves, whereas the concentration of monochloroacetic acid in the vapor phase is CA" % by weight. On the other hand, if the liquid temperature is TA, the equilibrium concentration of monochloroacetic acid is CA' % by weight according to the solid-liquid equilibrium curve, and thus supersaturation by (CA-CA') % by weight develops, and consequently monochloroacetic acid is crystallized out in an amount corresponding to (CA-CA') % by weight. Since the concentration of vaporized monochloroacetic acid is CA" % by weight, which is unsaturated according to the solid-liquid equilibrium curve, monochloroacetic acid or ice is not crystallized out at the condensation temperature.

When less than 5% by weight of water is added to a mixture of monochloroacetic acid and dichloroacetic acid on the basis of sum total of monochloroacetic acid, dichloroacetic acid and water, the concentration of dichloroacetic acid in the mother liquor is increased, and the purity of crystallized monochloroacetic acid is deteriorated. When more than 25% by weight of water is added to the mixture on the other hand, the concentration of monochloroacetic acid is less than Cc % by weight in FIG. 1, and consequently no supersaturation develops even by adiabatic cooling. That is, no monochloroacetic acid is crystallized out.

When adiabatic cooling is carried out under a pressure of more than 2,660 Pa, the level of the vapor-liquid equilibrium curves is raised towards the higher temperature side, that is, the equilibrium temperature is elevated, and no supersaturation develops even by adiabatic cooling. No monochloroacetic acid is crystallized out. When the adiabatic cooling is carried out under a pressure of less than 133 Pa on the other hand, the equilibrium temperature is lowered, and monochloroacetic acid or ice is crystallized out in the condensate when the vapor generated by the adiabatic cooling is condensed at the corresponding condensation temperature.

Thus, there is a criticality in the ranges for the ratio of water to be added and the pressure for adiabatic cooling. In the present invention, the range for a ratio of water to be added to a mixture of monochloroacetic acid and dichloroacetic acid is 5–25% by weight on the basis of sum total of monochloroacetic acid, dichloroacetic acid and water, and the range for the pressure for adiabatic cooling is 133–2,660 Pa.

Figure 2:
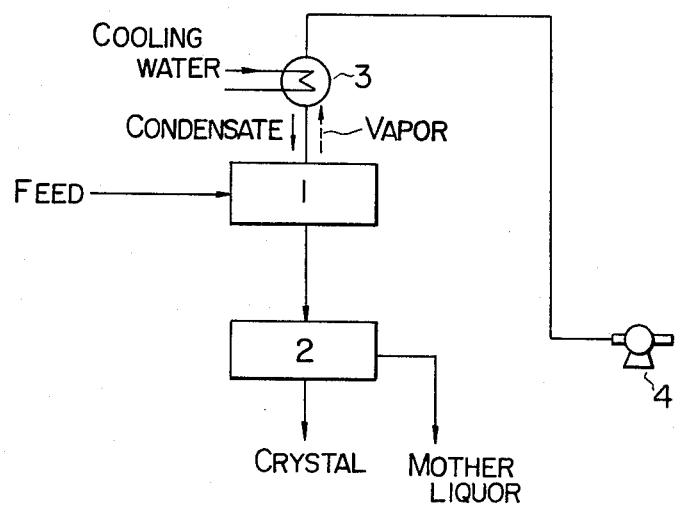
FIG. 2 is a flow diagram showing one mode of carrying out the present invention.

One embodiment of carrying out the present process is schematically shown in FIG. 2.

A solution containing monochloroacetic acid and dichloroacetic acid adjusted to the water content is fed to crystallizer 1 as feed, and subjected to adiabatic cooling in the crystallizer to crystallize out the monochloroacetic acid. Then, the resulting slurry is led to centrifuge 2 from the crystallizer to separate the crystals from mother liquor. On the other hand, the vapor generated in the crystallizer is condensed in condenser 3, and the resulting condensate is all refluxed to the crystallizer. The pressure in the crystallizer is reduced to a specific pressure by vacuum pump 2.

The present invention will be described in detail below, referring to Examples.

EXAMPLE 1

Crystallization of monochloroacetic acid was carried out according to the system shown in FIG. 2, where crystallizer 1 was a vertical cylindrical vessel having an inner diameter of 450 mm, a height of 1,900 mm and a liquid capacity of 130 l, provided with a draft tube having an inner diameter of 250 mm and a stirrer with a blade having a size of 200 mm, condenser 2 is a shell-and-tube type heat exchanger having a heat transfer area of 6 m², and vacuum pump 4 is provided with a steam-driven booster. The condensate in the condenser was all refluxed to the crystallizer.

130 l of a solution consisting of 90.4% by weight of monochloroacetic acid, 4.5% by weight of dichloroacetic acid, and 5.1% by weight of water was initially charged to crystallizer 1 and stirred by the stirrer at 1.7 rps, and subjected to adiabatic cooling while circulating the solution in the crystallizer at a rate of 50 m³/hour and gradually reducing the pressure in the crystallizer down to 2,130 Pa. After it was confirmed that monochloroacetic acid was crystallized out under a pressure of 2,130 Pa in the crystallizer at the corresponding temperature of 39° C., a solution of the same composition as initially charged, kept at 60°–65° C. was fed to the crystallizer at a rate of 40–45 l/hour, and the increment of the solution in the crystallizer was withdrawn as slurry to centrifuge 2 at a rate of 20–25 l at intervals 30 minutes. The slurry was centrifuged in the centrifuge to separate the monochloroacetic acid crystals from mother liquor. Washing of the separated crystals was not required. Operation was continued for 24 hours, and the results are given in Table. The monochloroacetic acid crystals had a purity of 99.5% and an average grain size of 0.31 mm.

EXAMPLE 2

Crystallization of monochloroacetic acid was carried out according to FIG. 2, using apparatuses of Example 1.

130 l of a solution consisting of 80.6% by weight of monochloroacetic acid, 12.0% by weight of dichloroacetic acid, and 7.4% by weight of water was initially charged into the crystallizer 1, stirred with a stirrer at 1.7 rps and subjected to adiabatic cooling while circulating the solution in the crystallizer at a rate of 50 m³/hour and gradually reducing the pressure in the crystallizer down to 1,730 Pa. After it was confirmed that monochloroacetic acid was crystallized out under a pressure of 1,730 Pa in the crystallizer at the corresponding temperature of 36° C., a solution of the same composition as initially charged, kept at 60°–65° C. was fed to the crystallizer at a rate of 40–45 l/hour, and the increment of the solution in the crystallizer was withdrawn as a slurry into centrifuge 2 at a rate of 20–25 l at intervals of 30 minutes. The slurry was centrifuged in the centrifuge to separate the monochloroacetic acid crystals from mother liquor. Washing of the separated crystals was not necessary. Operation was continued for 24 hours. The results are given in Table. The monochloroacetic acid crystals had a purity of 99.6% and an average grain size of 0.48 mm.

TABLE

| | Ex. 1 | Ex. 2 |
|---|---|---|
| Feed composition (% by weight) | | |
| Monochloroacetic acid | 90.4 | 80.6 |
| Dichloroacetic acid | 4.5 | 12.0 |
| Water | 5.1 | 7.4 |
| Feed rate (kg/hr) | 52 | 52 |
| Crystallizer pressure (Pa) | 2130 | 1730 |
| Crystallizer temperature (°C.) | 39 | 36 |
| Crystallizer circulation (m³/hr) | 50 | 50 |
| Operating supersaturation degree | | |
| Crystallized monochloroacetic acid (kg/hr) | 0.45 | 0.08 |
| Circulation rate (m³/hr) | | |
| Crystallized monochloroacetic acid (kg/hr) | 22.7 | 4.2 |
| Crystallized monochloroacetic acid | 0.31 | 0.48 |

TABLE-continued

|  | Ex. 1 | Ex. 2 |
| --- | --- | --- |
| average grain size (mm) | | |
| Crystallized monochloroacetic acid shape | Colummar | Colummar |
| Mother liquid composition (% by weight) | | |
|   Monochloroacetic acid | 83.0 | 78.9 |
|   Dichloroacetic acid | 7.9 | 13.1 |
|   Water | 9.1 | 8.0 |
| Slurry concentration (% by weight) | 43.6 | 8.0 |
| Crystallized monochloroacetic acid purity (% by weight) | 99.5 | 99.6 |

We claim:

1. A process for crystallizing monochloroacetic acid, which comprises adding 5-25% by weight of water to a mixture containing monochloroacetic acid and dichloroacetic acid as the main components on the basis of sum total of monochloroacetic acid, dichloroacetic acid, and water, and subjecting the mixture to adiabatic cooling at a pressure of 133-2,660 Pa.

2. A process according to claim 1, wherein the mixture is a solution containing 0-3% by weight of acetic acid, 90-99% by weight of monochloroacetic acid, and 1-6% by weight of dichloroacetic acid.

* * * * *

UNITED STATES PATENT AND TRADEMARK OFFICE
CERTIFICATE OF CORRECTION

PATENT NO. : 4,383,121
DATED : May 10, 1983
INVENTOR(S) : RYOJI SUGAMIYA ET AL

It is certified that error appears in the above-identified patent and that said Letters Patent is hereby corrected as shown below:

On the cover page, Item [73], change "Tsukishima Kaikai Co., Ltd." to --- Tsukishima Kikai Co., Ltd. ---.

Signed and Sealed this

Third Day of September 1985

[SEAL]

Attest:

DONALD J. QUIGG

Attesting Officer    Acting Commissioner of Patents and Trademarks - Designate